(12) United States Patent
Miljkovic

(10) Patent No.: US 6,696,419 B1
(45) Date of Patent: Feb. 24, 2004

(54) BORON COMPOUNDS AND COMPLEXES AS ANTI-INFLAMMATORY AGENTS

(76) Inventor: Dusan Miljkovic, 4655 Ramsay Ave., San Diego, CA (US) 92122

( * ) Notice: Subject to any disclaimer, the term of this patent is extended or adjusted under 35 U.S.C. 154(b) by 0 days.

(21) Appl. No.: 10/129,938

(22) PCT Filed: Nov. 14, 2000

(86) PCT No.: PCT/US00/31354

§ 371 (c)(1), (2), (4) Date: Jan. 7, 2003

(87) PCT Pub. No.: WO01/35966

PCT Pub. Date: May 25, 2001

Related U.S. Application Data

(60) Provisional application No. 60/166,938, filed on Nov. 19, 1999.

(51) Int. Cl.⁷ .......................... A61K 31/70; A61K 31/69
(52) U.S. Cl. ............................................. 514/23; 514/64
(58) Field of Search ..................................... 514/23, 64

(56) References Cited

U.S. PATENT DOCUMENTS

| | | | |
|---|---|---|---|
| 4,849,220 A | 7/1989 | Nielson et al. ............. 424/659 |
| 5,312,816 A | 5/1994 | Spielvogel et al. ............ 514/64 |
| 5,985,842 A | * 11/1999 | Miljkovic .................... 514/23 |
| 6,080,425 A | * 6/2000 | Miljikovic et al. ......... 424/450 |

* cited by examiner

Primary Examiner—Raymond Henley, III
(74) Attorney, Agent, or Firm—Rutan & Tucker

(57) ABSTRACT

Inflammation is affected by topical application of a boron containing compound/complex in which a central tetrahedral boron atom is covalently bound to four ligands. At least one of the ligands preferably includes an oxygen, nitrogen, carbon, or sulfur atom, and preferably all four ligands include at least one such atom. Preferred ligands are saccharides and amino acids, including fructose, sorbitol, mannitol, xylitol, sorbose, serine and threonine. Especially preferred ligands have a conformation with at least two hydroxyl groups, or one hydroxyl group and one amino group in a 1,2- and a 1,3-position relative to each other, providing a high association constant in the range of about 3,000 and about 20,000. The compounds/complexes are preferably provided in formulations which provide good transdermal delivery, including appropriate solvent systems, microemulsions, liposomes. Particularly targeted inflammations are those of the joints and skin, including bums such as sunburn.

20 Claims, 2 Drawing Sheets

BORON COMPOUND/COMPLEXES

TYPE I (4 monodentate ligands)

TYPE II (2 monodentate and 1 bidentate ligands)

TYPE IV (1 tridentate and 1 monodentate ligands)

TYPE III (2 bidentate ligands)

TYPE V (1 tetradentate ligand)

GENERAL FORMULAS OF THE ACTIVE BORON COMPOUNDS/COMPLEXES
(x,y,z,w - any hetero-atom excluding boron such as O, N, S, C, etc.)

BORON COMPOUNDS AND COMPLEXES AS ANTI-INFLAMMATORY AGENTS

This is a 371 of PCT/US00/31354 filed Nov. 14, 2000 which claims benefit of U.S. Provisional Application Ser. No. 60/166,938 filed Nov. 19, 1999.

FIELD OF THE INVENTION

The field of the invention is anti-inflammatory agents.

BACKGROUND OF THE INVENTION

Biological Activity And Use Of Boron Compounds

Boron compounds are known to show a variety of different biological activities. Very often, boron compounds show enzyme inhibitory activity, and thus boron compounds can inhibit a number of enzymes alone or in a mixture with various co-inhibitors. For example, borates inhibit L-amino acid oxidase in a mixture with butanedione by interacting with the arginine residue in the active site. (Christman M F, Cardenas J M: Experientia 38 (5): 537–538 (1982)).

Similarly, borates and butanedione inhibit citrate/isocitrate-hydro-lyase, EC 4.2.1.3, again by interacting with the arginine residue from the active site. (Gawron O, Jones L: Biochem Biophys Acta 484 (2): 453–464 (1977)). Also, 2,3-butanedione or 1,2-cyclohexanedione in the presence of borates interact specifically with the guanidino group from arginine, and this fact was used for determination of arginine residues in the active site of the examined enzymes. In this way Dietl, T. and Tschesche, H . (Hoppe Seylers Z Physiol Chem: 357 (5): 657–665 (1976)) proved arginine residue is present in the active site of proteinases.

Borates (at low concentration) are also known to inhibit glyceraldehyde-3-phosphate dehydrogenase from human, pig and rabbit muscle. However, in greater concentration (above 6 mM) borates inhibit esterase and acetylphosphatase activities. (Wolny M: Eur J Biochem 80 (2): 551–556 (1977)).

An interesting biological activity of borates was noticed in the case of palytoxin induction of the histamine release from rat mast cells. In the presence of borates the activity of palytoxin was increased ten times (Chhatwal G S, Ahnert-Hilger G, Beress 1, Habermann E: Int Arch Allergy Appl Immunol 68 (2): 97–100 (1982)).

Borates inhibit methylation of catechol estrogen and pyrocatechol by catechol-O-methyltransferase (Beattie J H, Weersink E: J Inorg Biochem 46 (3): 153–160 (1992)).

Several naturally occurring antibiotics contain boron as an essential structural element (such as boromycin, an anti-HIV antibiotic (Kohno J, et al: Biosci Biotechnol Biochem (Japan) 60(6), 1036–7 (1996), or tetralons, new boron-containing antibiotics from a myxobacterium, Sorangium cellulosum (Irschik H, Schummer D, Gerth K, Hofle G, Reichenbach H: J Antibiot (Tokyo) (Japan), 48 (1), 26–30 (1995)).

Borates and some of their organic complexes are experimentally used in surgery as agents which promote healing of open wounds (Humzah M D, Marshall J, Breach N M: J R Coll Surg Edinb (England) 41(4), 269–70 (1996); McCowan M, Aitken F: J Wound Care (England), 6(5), 248–249 (1997); Bliss M R: J Wound Care (England) 6(5), 248–249 (1997)).

Larvicidal effects of ingestion of boric acid and disodium octaborate tetrahydrate by cat fleas was recently described by Hinkle N C, Koehler P G, and Patterson R S in J Med Entomol (United States), July 1995,32(4), p 424–7.

Some specific organoboron compounds (such as cyanotriphenylborate) were shown to be subtype-specific blockers of glycine receptor chloride channels (Rundstrom N, Schmieden V, Betz H, Bormann J, Langosch D: Proc Natl Acad Sci USA (United States), 91(19), 8950–4 (1994)).

A very important biological behavior of certain boron compounds is their interaction with Ca-metabolism. Namely, it has been noticed (Benderdour M, Hess K, Dzondo-Gadet M, Dousset B: Biochem Biophys Res Commun 234 (1), 263–8 (1997)) that boric acid itself, acting upon a pelvic cartilage of chick embryo, induced release of proteoglycans, collagen and other proteins, but at the same time strongly decreased their intracellular synthesis. However, surprisingly enough, boric acid in the presence of a great molar excess of glucose did not decrease intracellular biosynthesis of proteins, but still induced efficiently their intensive secretion. The effect can not be ascribed to a boron toxicity, since the cell membranes were intact (observed by electronic microscopy) and the cells were secretory. It was assumed that boron interacted actively with Ca-metabolism (see, in addition to this article, Nielsen F, Muller L, Gallgher S: J Trace Elem Exp Med 3, 45–54 (1990); Nielsen F H: FASEB 5, 2661–7 (1991)). Benderdour et al postulated that boric acid or its glucose complex can inhibit serine/threonine phosphatases.

Specific biological calcium-boron interaction is also supported by a work of T. Maruyama et al (J Biochem (Tokyo), 122(3), 498–505 (1997)) who showed that 2-aminoethoxydiphenyl borate (2 APB) inhibited Ins (1,4,5) P3-induced $Ca^{2+}$ release from rat cerebellar microsomal preparations. At the same time, addition of 2 APB to the extracellular environment inhibited the cytosolic $Ca^{2+}$ rise in intact cells such as human platelets and neutrophiles stimulated by thrombin or leukotriene B4 (LTB4).

Anti-inflammatory Effects

The present applicant has evidence showing that Boron has and anti-inflammatory action when taken as a nutritional supplement. Supplemental boron is known in many different forms. As over-the-counter supplements, for example, boron is marketed as calcium borogluconate (Now Foods, Glendale Hts., Ill.), and as boron citrate, aspartame and glycinate chelates (Twin Laboratories, Inc., Ronkonkoma, N.Y.). U.S. Pat. No. 4,849,220 to Hunt, issued Jul. 18, 1989, describes the addition of boric acid ($H_3BO_3$) to the diet of postmenopausal women, and U.S. Pat. No. 5,312,816 to Spielvogel et al. describes dietary supplementation with Lewis-acid base boron adducts. Boron has also been given as a simple salt, such as sodium borate, or sodium tertraborate decahydrate.

Unfortunately, these known forms of boron supplementation have noticeably undesirable side effects, rendering the known forms of boron supplementation somewhat undesirable as anti-inflammatory agents. First, the known forms either contain or are readily hydrolyzed in the gut to boric acid. Boric acid is reactive, and tends to accumulate in tissues other than bone or joint. Second, the amount of boron made available by known supplementation is extremely high compared with normal blood values. A typical boron supplement, for example, may make almost 3 mg of elemental boron available to the tissues within a half hour after ingestion, which is about 14 times the normal total blood boron of 213 $\mu$g. (Hunt, C. D., et al., "RDA Workshop: New Approaches, Endpoints and Paradigms for RDAs of Mineral Elements", *American Institute of Nutrition*, 1996, pp 2441S–2451S). Third, while there is a mechanism which limits boron absorption from foods when boron intake is high, (Hunt, C. D., et al., "RDA Workshop . . . ", supra), that mechanism likely does not act to prevent the almost immediate availability of boron from currently known supplements. Fourth, it has been estimated that less than a quarter of the population takes vitamin/mineral supplements on a daily basis, so that the known forms of supplementation are unlikely to reach a high percentage of the population.

Thus, there is still a need to provide in forms and formulations for use as an anti-inflammatory agent.

SUMMARY OF THE INVENTION

The present invention provides methods and compositions in which boron compounds/complexes having a central tetrahedral boron atom, covalently bound to four ligands (of either identical or different nature), are utilized to provide anti-inflammatory effects.

Specifically included among the contemplated anti-inflammatory effects are reduction of inflammation of knees, fingers and other joints, reduction of inflammation from insect bites and other localized traumas to the skin, is reduction of scar tissue and improved wound healing. One particularly useful indication for topical treatment is sunburned or otherwise burned skin.

In one aspect of preferred embodiments at least one of the ligands is contemplated to include an oxygen, nitrogen, carbon or sulfur atom, and in more preferred embodiments all four ligands are contemplated to include an oxygen, nitrogen, carbon or sulfur atom.

In another aspect of preferred embodiments, boron is complexed with a saccharide or an amino acid having at least two hydroxyl groups, or one amino- and one hydroxyl group in 1,2- or 1,3-position to each other. Such a spatial arrangement allows formation of stable five- or six-membered rings consisting of one boron atom, two hetero-atoms and 2 or 3 carbon atoms. Such complexes may advantageously comprise fructose, sorbitol, mannitol, xylitol, sorbose, serine or threonine. In its complexes boron is bound more or less tightly to hetero-atoms.

Quantitatively speaking, the stability of boron complexes is contemplated to be proportional to their association constants, and in yet another aspect of the invention, preferred complexes have association constants of at least 50, and more preferred complexes have an association constant between 3,000 and 20,000.

In yet another aspect of this invention, acidic boron complexes may be further converted to salts having sodium, potassium, magnesium or calcium as a counter ion (cation). However, one can successfully used other non-toxic and non-irritating cations such as ammonium, protonated amines, or quaternary ammonium cations.

In yet another aspect of this invention, an active boron compound/complex is included in a suitable cosmetic formulation wherein the compound/complex is provided in a suitable solvent system, a microemulsion form, or a suitable liposome form. These formulations may advantageously contain other ingredients that are also non-toxic and non-irritating to the skin. The composition is also preferably adapted for efficient penetration through the skin stratum corneum barrier when applied topically.

Various objects, features, aspects and advantages of the present invention will become more apparent from the following detailed description of preferred embodiments of the invention, along with the accompanying drawing.

DETAILED DESCRIPTION

Figure 1:
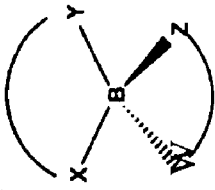
FIG. 1 depicts generic chemical structures of boron compounds/complexes according to the present invention.
Figure 1:
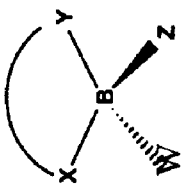
Figure 1:
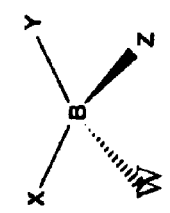
Figure 1:
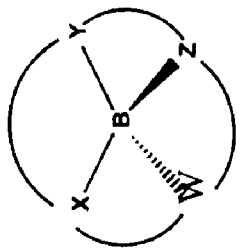
Figure 1:
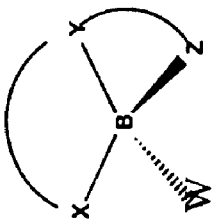

According to the present invention, boron compounds and complexes containing sugars, sugar polyols, amino acids and other non-toxic boron specific ligands, may be used as anti-inflammatory agents.

In one aspect of preferred embodiments, Boron compounds/complexes contemplated herein may be taken orally as nutritional supplements, or may be placed in solution and applied topically to the skin.

In another aspect of preferred embodiments, Boron compounds/complexes contemplated herein have a tetrahedral boron atom covalently bound to four hetero-atoms which can be identical or different from one another. As used herein, the term hetero-atom means any chemical element except boron. Preferably, hetero-atoms include oxygen, nitrogen, carbon and sulfur, but are also contemplated to include hydrogen, and non-metallic elements from groups IVA, VA, VIA and VIIA of the periodic table.

These contemplated boron compounds/complexes can be natural, synthetic, or some combination of natural and synthetic. Thus, it is contemplated to use boron complexes which exist in nature such as glyco-borates and sugar polyols complexed with borates, both of which are often found in fruits. For practical reasons, these naturally occurring boron compounds are best synthesized, although theoretically they could be extracted from natural sources.

Boron compounds/complexes employed according to the present invention can be prepared in any suitable manner. In an exemplary synthesis, sodium borate/tetraborate is treated with two molar equivalents of sugar polyol (preferably mannitol or xylytol), or two molar equivalents of an amino acid (preferably serine or threonine), in an aqueous solution. Generally, isolation of the formed complex is not necessary since the aqueous solution is immediately used for the final formulation of the product (such as in a liposome or microemulsion form). However, if necessary, the isolation of the boron compound/ complex is readily achievable. In these cases, usually, an excess of ethanol is added to aqueous solution of a boron compound/complex, whereupon the boron complex crystallizes out. The solid product can be recrystallized if needed including aqueous and non-aqueous carriers.

It is also contemplated that other ligands (mono-, di- and/or poly-valent), in the corresponding molar ratio to the starting boron compound, can be simply mixed in an appropriate solvent (water, acetone, dioxan, tetrahydrofuran, etc), whereupon the complex directly crystallizes out, or stays in a solution.

Regarding metal ions which charge neutralize the boron anionic complex, one can use any of a variety of non-toxic metallic cations, such as sodium, potassium, calcium, or magnesium. However, one can successfully use ammonium cation, protonated amines, as well as quaternary ammonium cations.

Generally speaking I contemplate that the higher the association constant of the boron complex, the less toxic is the complex, and the more advantageous are its biological properties. In a quantitative sense, association constants at or above about 50 are usable, although ones of over 1,000 are preferable. In the most favorable cases, association constants between about 3,000 and about 20,000 are especially beneficial.

Figures 2A, 2B:
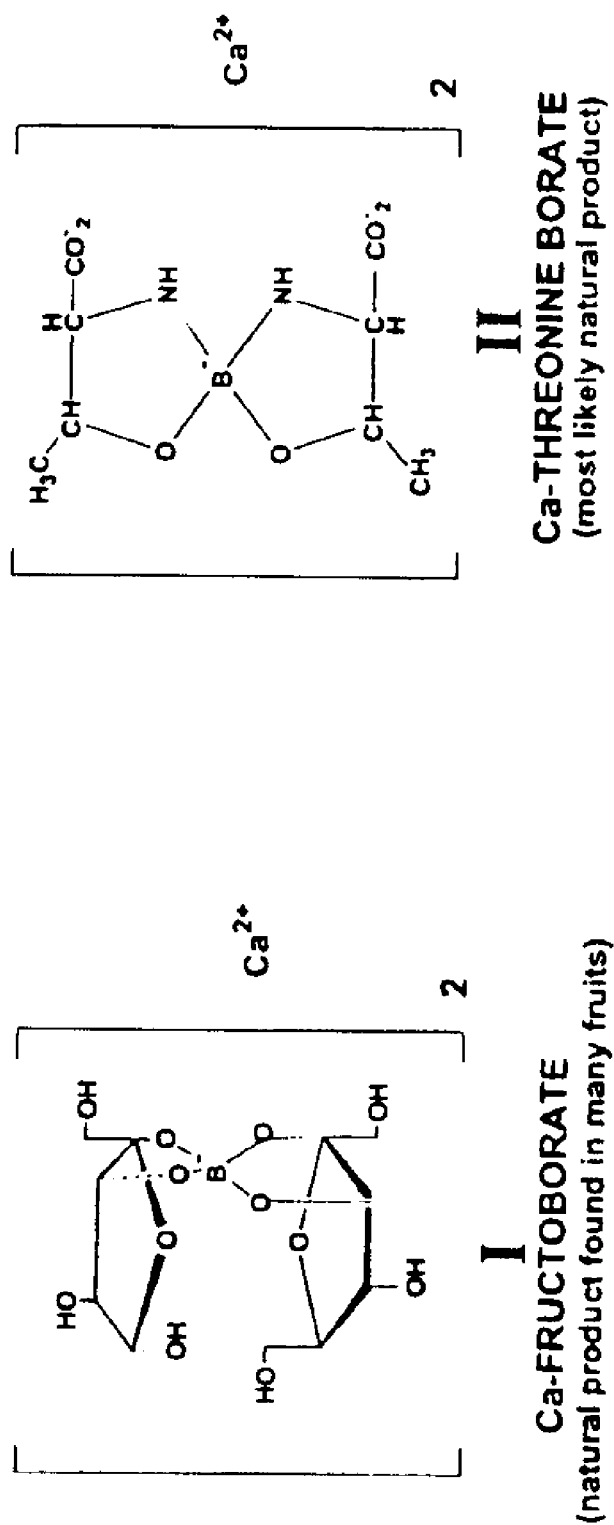
FIGS. 2A and 2B are chemical structures depicting particularly preferred compounds, calcium fructo-borate complex, and calcium threonine borate complex.

The general structure of boron compounds suitable for anti-inflammatory effects is depicted in FIG. 1. Residues W, X, Y and Z may be the same as, or different from one another, and are contemplated to include any suitable hetero-atom. The five-membered rings are preferred over six-membered rings, and the six-membered rings are preferred over hepta-membered ring, and so forth. FIG. 2A depicts a particularly preferred compound, calcium fructo-borate complex, illustrated in one of several possible structural conformations. FIG. 2B depicts another particularly preferred compound, calcium threonine borate complex.

Contemplated formulations of boron compounds/complexes contemplated herein may advantageously involve a solution or emulsion of the active material in water, aqueous buffer, a mixture of water and an organic solvent allowed in topical skin treatment (such as ethanol, glycerol, etc), organic non-toxic and non-irritating solvents, or macro- and micro-emulsion forms, liposome forms, or in any other suitable carrier(s) for topical application. Particularly contemplated carriers are liposome and microemulsion formulations, and at present the most preferred carriers are emulsions of a bile acid salt (such as sodium taurocholate) and a soybean oil such as soybean phosphatidyl choline (SPC). Such formulations are contemplated to efficiently penetrate the skin stratum corneum barrier and reach the stratum spinosum, stratum basalis, and dermis. As used herein, the term "solution" is used a broad lay sense to mean any substance dispersed in a carrier. Thus, according to the definition used herein, boron compound/complex solutions include mixtures of boron containing compounds and/or complexes in all manner of solvents, whether homogeneously or non-homogeneously dispersed, completely or partially solvated, suspended, emulsified, or dispersed in any other manner. Boron compound/complex solutions thus also include all possible carriers.

Preferred concentrations of solutions/emulsions have about $10^{-6}$ to 10 weight % of boron, with solutions/emulsions containing 1–5 mg of B/ml. contemplated to be particularly suitable for anti-inflammatory purposes. Such solutions/emulsions are contemplated to be rubbed onto the skin twice per day, morning and evening, preferably after a shower or bath. Other contemplated protocols include applications of greater or lesser frequency, such as daily, every-other day, weekly, or bi-weekly schedules.

A particularly preferred method of application is partial or full immersion in a bath. Thus, boron compounds/complexes contemplated herein may form all or part of bath salts, which can be added to a bath or other container of water and used for soaking in a manner analogous to that now known for Epsom Salts (magnesium sulfate). Such immersion may then advantageously be followed by topical application of a cream at or near sites of particular inflammation.

Without being limited to the validity or applicability of any particular mechanism or mode of action, it is contemplated that the boron compounds/complexes contemplated herein affect inflammation through interaction with a broad range of enzymes and enzyme systems, as opposed to targeting a single enzyme or enzyme system. Such systems are present to a greater or lesser extent across a broad range of animals, and it is thus contemplated that the inventive subject matter is broadly applicable to humans, other mammals, as well as other animals.

Also, without being limited to particular objects and advantages, it is contemplated that there are numerous potential advantages of the methods and compositions discussed herein. Among other things, selected boron compounds/complexes from this invention, and in particular ones containing natural sugars, sugar polyols, and amino acid, are considerably less toxic than boric acid and its simplest derivatives, and are thus safer than boric acid itself or its simple derivatives for prolonged topical applications, including long term anti-inflammatory effects on joints. Another advantage is that many of the boron compounds/complexes contemplated herein are stable at ambient temperatures, storable in their suitable formulations for a long time and are commercially readily available. Still another advantage is that many of the boron compounds/complexes contemplated herein are expected to show multifunctional synergistic biological activity. This represents a great advantage in relation to other previously described anti-inflammatory agents, all of which were specifically active towards one particular enzyme.

EXPERIMENTS

General Remarks

When synthesizing boron compounds/complexes according to the present disclosure, one should generally follow accepted rules of chemical synthesis. Thus, if a ligand contains only one hetero-atom in its B-binding site, one takes four or more molar equivalents of it in respect to one molar equivalent of the starting boron compound. Further, if a ligand contains two or three hetero-atoms in its B-binding sites, one takes two or more molar equivalents of it in respect to one molar equivalent of the starting boron compound. Still further, if a ligand contains four or more hetero-atoms in its B-binding sites, one takes one or more equivalents of the ligand to one molar equivalent of the starting boron compound. Of course, the molar equivalent of the starting boron compound corresponds to its molecular formula if it contains one boron atom in it. If molecular formula contains more than one boron atom one divides molecular formula with a number of boron atoms containing in it. For example, if one starts with sodium tetraborate decahydrate, its molecular formula should be divided by four to obtain its molar equivalent.

General Preparation Procedure Of Boron Compounds/Complexes

As a rule, the selected ligand, in the corresponding or slightly higher molar ratio to the starting boron compound and the starting boron compound (most often boric acid or borax), is mixed in water to make a rather concentrated solution (usually in the range from 10 to 30%). The reaction mixture is stirred or shaken at room temperature for 0.5 to 1 hour, whereupon all solid components go completely to a solution. If boric acid is used, then subsequent neutralization is needed, such as with $NaHCO_3$, $KHCO_3$, $CaHCO_3$, etc.

Reaching this point, one can proceed further according to one of the two possibilities:
a) using the prepared solution (in undiluted or diluted form) for the final formulation preparation, or if one needs pure and chemically better defined complexes,
b) using the prepared solution for the isolation and purification of the desired B-complex.

In carrying out detailed experimental work, one uses standard procedures and techniques that are familiar to a person trained in the field of inorganic/organic synthetic preparations. However, for illustrative purposes bellow given examples should clarify certain important experimental details.

EXAMPLE 1

Calcium Boro-Mannitol (Calcium Mannitolo-Borate)

Boric acid (1.24 g; 20 mmoles) and mannitol (7.28 g; 40 mmoles) are dissolved in water (20 ml) at 60°–70° C. After cooling down to room temperature, solid calcium carbonate (1 g; 10 mmoles) is gradually added the solution. During the addition of calcium carbonate carbon dioxide is evolved. When all calcium carbonate is dissolved and carbon dioxide evolution ceased (which at lasts about 30 minutes), one adds ethanol (80 ml). Viscous (semi-solid) heavy layer separates out and the upper aqueous-ethanolic solution is decanted off. A new portion of ethanol is added (80 ml), whereupon, on stirring at room temperature for a while, the crystalline complex separated out.

The same is filtered off and washed with ethanol (40 ml). After drying the complex in vacuum desicator, one obtains pure crystalline Ca-mannito-borate (7 g; 90% of theoretical yield). A similar procedure can be carried out using other cations, such as those of magnesium and potassium, and such may be preferred to avoid phosphates in the skin precipitating the calcium.

EXAMPLE 2

Sodium Serine/Borate Complex (In Aqueous Solution)

Sodium tetraborate (0.804 g; 4 mmoles) and serine (3.2 g; 32 mmoles) are mixed in water (ml) at room temperature. After stirring or shaking for 0.5 to 1 hour at room temperature, all components go into solution. The final concentration is adjusted to the desired level (usually 2–4 mg B/ml).

EXAMPLE 3

Liposome Formulation Of Calcium Fructo-Borate

Calcium fructo-borate (g) is dissolved in distilled water (ml). Separately, phosphatidyl choline (PC) in chloroform is evaporated at room temperature in vacuum with a rotary evaporator at room temperature to provide a uniform transparent lipid film.

The water solution of calcium fructo-borate is added at once to a lipid PC-film. After shaking the mixture for 2 hours at 37 C, and sonicating the mixture for an additional 0.5 hour at room temperature, preparation of the calcium fructoborate liposome formulation is finished.

What is claimed is:

1. A method of treating inflammation in an individual, comprising:
    selecting a formulation demonstrated to reduce inflammation when applied topically, said formulation including a boron containing structure having a central tetrahedral boron atom covalently bound to four ligands; and
    applying the formulation to an area of skin of the individual according to a protocol sufficient to reduce the inflammation.

2. The method of claim 1 wherein at least one of the ligands includes an atom selected from the group consisting of oxygen, nitrogen, carbon, and sulfur.

3. The method of claim 1 wherein each of the four ligands includes an atom selected from the group consisting of oxygen, nitrogen, carbon, and sulfur.

4. The method of claim 1 wherein the boron atom is bound to a ligand to form a stable five- or six-membered ring comprising the boron atom, two hetero-atoms and 2 or 3 carbon atoms.

5. The method of claim 4 wherein the ligand comprises a saccharide.

6. The method of claim 4 wherein the ligand comprises an amino acid.

7. The method of claim 4 wherein the ligand is selected from the group consisting of fructose, sorbitol, mannitol, xylitol, sorbose, serine and threonine.

8. The method of claim 4 wherein the ligand has a conformation having at least two hydroxyl groups in at least one of a 1,2- and a 1,3-position relative to each other.

9. The method of claim 4 wherein the ligand has a conformation having at least one amino- and one hydroxyl group in at least one of a 1,2- and a 1,3-position relative to each other.

10. The methods of any one of claims 1–9 further comprising a boron complex having an association constant of at least 50.

11. The methods of any one of claims 1–9 further comprising a boron complex having an association constant of between about 3,000 and about 20,000.

12. The methods of any one of claims 1–9 wherein the boron containing structure comprises a salt.

13. The methods of any one of claims 1–9 wherein the boron containing structure includes a cation selected from the group consisting of sodium, potassium, magnesium and calcium.

14. The methods of any one of claims 1–9 wherein the boron containing structure includes a cation selected from the group consisting of ammonium, and a protonated amine.

15. The methods of any one of claims 1–9 wherein the formulation comprises at least one of a solvent system, a microemulsion, and a liposome.

16. The methods of any one of claims 1–9 wherein the boron containing structure comprises a salt, and the formulation comprises at least one of a solvent system, a microemulsion, and a liposome.

17. The method of claim 1 wherein the boron containing structure comprises calcium fructo-borate.

18. The method of any one of claims 1–9 or 17 wherein the inflammation comprises inflammation of a joint.

19. The method of any one of claims 1–9 or 17 wherein the inflammation comprises inflammation of the skin.

20. The method of any one of claims 1–9 or 17 wherein the inflammation comprises a burn of the skin.

* * * * *